(12) United States Patent
Creasy, II

(10) Patent No.: US 12,274,680 B2
(45) Date of Patent: Apr. 15, 2025

(54) TREATMENT OF BENIGN PROSTATIC HYPERTROPHY WITH CAPSINOIDS

(71) Applicant: George William Creasy, II, Glen Gardner, NJ (US)

(72) Inventor: George William Creasy, II, Glen Gardner, NJ (US)

( * ) Notice: Subject to any disclaimer, the term of this patent is extended or adjusted under 35 U.S.C. 154(b) by 155 days.

(21) Appl. No.: 18/188,796

(22) Filed: Mar. 23, 2023

(65) Prior Publication Data

US 2024/0082178 A1    Mar. 14, 2024

Related U.S. Application Data

(60) Provisional application No. 63/375,455, filed on Sep. 13, 2022.

(51) Int. Cl.
| | | |
|---|---|---|
| *A61K 31/165* | (2006.01) | |
| *A61K 9/00* | (2006.01) | |
| *A61K 31/231* | (2006.01) | |
| *A61K 31/357* | (2006.01) | |
| *A61P 13/10* | (2006.01) | |

(52) U.S. Cl.
CPC .......... *A61K 31/165* (2013.01); *A61K 9/0053* (2013.01); *A61K 31/231* (2013.01); *A61K 31/357* (2013.01); *A61P 13/10* (2018.01)

(58) Field of Classification Search
CPC .. A61K 31/165; A61K 9/0053; A61K 31/231; A61K 31/357; A61P 13/10; A01H 6/822
See application file for complete search history.

(56) References Cited

U.S. PATENT DOCUMENTS

| | | |
|---|---|---|
| 5,843,016 A | 12/1998 | Lugnani et al. |
| 6,048,888 A | 4/2000 | Zisapel |
| 6,200,573 B1 | 3/2001 | Locke |
| 6,376,488 B1 | 4/2002 | Basha et al. |
| 6,410,554 B1 | 6/2002 | Broten et al. |
| 7,122,173 B2 | 10/2006 | Yamagata et al. |
| 7,446,121 B2 | 11/2008 | Pfefferkorn |
| 7,556,828 B2 | 7/2009 | Zhang et al. |
| 9,420,817 B2 | 8/2016 | Ebihara et al. |
| 9,579,364 B2 | 2/2017 | Kleinberg et al. |
| 9,682,115 B2 | 6/2017 | Seipel |
| 10,010,534 B2 | 7/2018 | Cox et al. |
| 2004/0132728 A1 | 7/2004 | Pullen et al. |
| 2009/0186896 A1 | 7/2009 | Ulbrich et al. |
| 2010/0204319 A1* | 8/2010 | Archibald ............... A61P 13/10 514/515 |
| 2010/0210668 A1 | 8/2010 | Choi et al. |
| 2010/0331361 A1 | 12/2010 | Kakizaki et al. |
| 2012/0172302 A1 | 7/2012 | Petri et al. |
| 2021/0046140 A1 | 2/2021 | Hwang et al. |
| 2021/0161642 A1 | 6/2021 | Jen et al. |
| 2022/0117971 A1 | 4/2022 | Mudd, Jr. et al. |

FOREIGN PATENT DOCUMENTS

| | | | |
|---|---|---|---|
| CN | 114042068 A * | 2/2022 | |
| HU | 0400847 A2 * | 9/2005 | |
| HU | P0400847 A2 * | 9/2005 | |
| WO | WO-2009021058 A2 * | 9/2009 | ........... A61K 31/137 |

* cited by examiner

*Primary Examiner* — Danah Al-Awadi
*Assistant Examiner* — Alison Azar Salamatian
(74) *Attorney, Agent, or Firm* — Dunlap Bennett & Ludwig, PLLC; Anna L. Kinney

(57) ABSTRACT

A method for reducing bladder outlet obstruction and/or self-catheterization frequency of a male patient with bladder outlet obstruction (BOO) due to benign prostatic hypertrophy (BPH) is disclosed. The method comprises orally administering to a male patient suffering from BOO due to BPH an effective amount of an active ingredient selected from a capsinoid mixture, enabling the patient suffering from BOO due to BPH to reduce BOO and/or the self-catheterization frequency.

10 Claims, No Drawings

TREATMENT OF BENIGN PROSTATIC HYPERTROPHY WITH CAPSINOIDS

CROSS REFERENCE TO RELATED APPLICATION

This nonprovisional application is based on provisional application U.S. Ser. No. 63/375,455 filed Sep. 13, 2022, hereby incorporated by reference in its entirety.

FIELD

The present subject matter is directed, in general, to the field of benign prostatic hypertrophy (BPH), more particularly to a method of reducing bladder outlet obstruction, and even more particularly to a method of reducing the frequency of self-catheterization in cases of bladder outlet obstruction due to BPH.

BACKGROUND

Benign prostatic hypertrophy (BPH), also called prostate enlargement, is a noncancerous increase in size of the prostate gland. Symptoms may include frequent urination, trouble starting to urinate, weak stream, inability to urinate also called bladder outlet obstruction (BOO), or loss of bladder control. Complications can include urinary tract infections, bladder stones, and chronic kidney problems.

The cause is unclear. Risk factors include a family history, obesity, type 2 diabetes, not enough exercise, and erectile dysfunction. Medications like pseudoephedrine, anticholinergics, and calcium channel blockers may worsen symptoms. The underlying mechanism involves the prostate pressing on the urethra, thereby making it difficult to pass urine out of the bladder. Diagnosis is typically based on symptoms and examination after ruling out other potential causes.

Treatment options include lifestyle changes, medications, a number of non-excisional surgical procedures, and excisional surgery. In those with mild symptoms: weight loss, exercise, and decreasing caffeine intake are recommended, although the quality of the evidence for exercise is low. In those with more significant symptoms, medications may include alpha blockers such as terazosin or 5α-reductase inhibitors such as finasteride. Intraurethral balloon compression of the prostate can provide temporary relief of BOO. Self-catheterization can also overcome the occasional BOO symptoms. Surgical removal of part of the prostate may be carried out in those who do not improve with other measures. Phytotherapies that have been studied, such as saw palmetto, have not been shown to help.

About 105 million men are affected globally. BPH typically begins after the age of 40. Half of males aged 50 and over are affected. After the age of 80, that figure climbs to as high as about 90% of males affected. Although prostate specific antigen levels may be elevated in males with BPH, the condition does not increase the risk of prostate cancer.

BPH is the most common cause of lower urinary tract symptoms (LUTS), which are divided into storage, voiding, and symptoms which occur after urination. Storage symptoms include the need to urinate frequently, waking at night to urinate, urgency (compelling need to void that cannot be deferred), involuntary urination, including involuntary urination at night, or urge incontinence (urine leak following a strong sudden need to urinate). Voiding symptoms include urinary hesitancy (a delay between trying to urinate and the flow beginning), intermittency (not continuous), involuntary interruption of voiding (BOO), weak urinary stream, straining to void, a sensation of incomplete emptying, and uncontrollable leaking after the end of urination. These symptoms may be accompanied by bladder pain or pain while urinating (dysuria).

Bladder outlet obstruction (BOO) can be caused by BPH. Symptoms are abdominal pain, a continuous feeling of a full bladder, frequent urination, acute urinary retention (inability to urinate), pain during urination (dysuria), problems starting urination (urinary hesitancy), slow urine flow, starting and stopping (urinary intermittency), and nocturia.

BPH can be a progressive disease, especially if left untreated. Incomplete voiding results in residual urine or urinary stasis, which can lead to an increased risk of urinary tract infection.

Hormones, diet, and aging of tissues are among the proposed etiologies of BPH.

The clinical diagnosis of BPH is based on a history of LUTS (lower urinary tract symptoms), a digital rectal exam, and exclusion of other causes of similar signs and symptoms. The degree of LUTS does not necessarily correspond to the size of the prostate. An enlarged prostate gland on rectal examination that is symmetric and smooth supports a diagnosis of BPH. However, if the prostate gland feels asymmetrical, firm, or nodular, this raises concern for prostate cancer.

Validated questionnaires such as the American Urological Association Symptom Index (AUA-SI), the International Prostate Symptom Score (I-PSS), and more recently the UWIN (urgency, weak stream, incomplete emptying, and nocturia) score are useful aids to making the diagnosis of BPH and quantifying the severity of symptoms.

Once diagnosed and during the "wait and watch" period of non-surgical approaches, several dietary adjustments are recommended. There are lists of foods and additives to 'take' and lists of foods and additives to 'avoid.' The foods and additives to 'take' include: salmon, tomatoes, berries, broccoli, nuts, citrus, and onions/garlic. The foods and additives to 'avoid' include: red meat, dairy, caffeine, alcohol, and sodium. It is noteworthy that the recommendations are silent as to spicy peppers.

It is important here to distinguish between BOO due to BPH and the unrelated condition of Overactive/Irritable Bladder (OAB). Some of the symptoms of BOO due to BPH overlap with those of OAB, but the cause behind each is quite different as are the treatments. One common symptom shared by both BPH and OAB is incontinence. In BPH, the incontinence is due to a large volume of urine that is unable to be voided due to outlet obstruction; in OAB, the incontinence is due to a small volume of urine in a bladder which is unable to expand to normal capacity. One of the treatments for the constricted bladder in OAB is the temporary installation of a concentrated solution of capsaicin or a capsaicin agonist/analogue to accomplish two objectives: first, expand the constricted OAB bladder; and second, inhibit the bladder muscle from contracting. This type of capsaicin installation therapy is not appropriate for BOO due to BPH because neither of these mechanisms of treatment is appropriate in BOO due to BPH. Those skilled in the art know that capsaicin installation therapy can worsen BOO due to BPH. In fact, a placebo-controlled trial of an intravesical installation of a capsaicin agonist failed to improve both urine residual and urine flow, both of which are in need of improvement in the BOO due to BPH patient. A recent article on bladder health advises the avoidance of spicy foods as they may worsen urinary retention, making it difficult to fully empty your bladder similar to the effect of caffeinated or acidic foods and beverages. The understanding for those skilled in the art is that capsaicin and capsaicin agonists/analogues are not helpful and may worsen BOO due to BPH.

Published Patent Application No. US 2010/0204319 to Archibald mentions both BPH and capsaicin. That application is directed to the discovery of a synergy between broccoli (sulforaphanes) and capsicum plants (capsaicin). The claimed synergy between broccoli and capsicum plants improves bladder function in the treatment of BPH. The ratio of the claimed agents that results in the disclosed benefit is in the range of 10:1 to 100:1, for broccoli to capsicum. According to the publication, both the broccoli and the capsicum plants are finely ground before mixing at the specified ratios and administered by capsule. In the publication, the exceedingly small dose of capsicum synergistically enhances the sulforaphane in the broccoli to improve bladder function in BPH patients and this can be concluded from several prior art facts: first, capsaicin installation that is beneficial to OAB patients does not improve residual or flow as would be needed in BPH patients; second, the teaching of those skilled in the art is for BPH patients to avoid spicy foods (i.e.—capsicum plants). On the other hand, sulforaphanes are known to be beneficial to BPH patients and broccoli and other sulforaphane containing foods are widely recommended in the diet of BPH patients. Taken together, the exceedingly small dose of capsicum with an exceptionally large dose of broccoli (up to 100:1) results in a synergy that enhances the effect of the sulforaphane in the broccoli. This synergy was not described prior to 17 Oct. 2006.

More recent patents relating to BPH include U.S. Pat. No. 6,376,488 to Basha, U.S. Pat. No. 7,446,121 to Pfefferkorn, U.S. Pat. No. 9,579,364 to Kleinberg, and 10,010,534 to Cox. The Basha patent describes an alpha-adrenergic compound. Basha, at column 2, described the incidental clinical observation that urinary incontinence developed in women during antihypertensive treatment with prazosin (T. Thien, K. P. Delacre, F. M. J. Debruyne, R. A P. Koene, Br. Med. Journal, 622-623(1978)) and the experimental work of Caine (op cit.) contributed to the recognition of the potential role of selective alpha-adrenoreceptor blockade in diseases of the lower urinary tract. Subsequent studies by several groups have documented the functional role of alpha-1 adrenoreceptors relative to alpha-2 adrenoreceptors in the stromal compartment of the prostate, thereby providing a putative molecular basis for the use of specific alpha-1 adrenoreceptor blockers in the non-surgical management of BPH (C. R. Chapple, M. L. Aubry, S. James, M. Greengrass, G. Burnstock, R. T. Turner-Warwick, Br. J. Urol. 63: 487-496 (1989)). Clinical efficacy of alpha-1 antagonists in BPH has been demonstrated with several non-selective alpha-1 blockers, including terazosin30 (Hytrin®), prazosin, and doxazosin. Treatment periods as short as two to four weeks with alpha-1 adrenoreceptor blockers have shown objective improvements in the mean and maximum urinary flow rates (14-96%) with subjective improvements in patients' symptom scores (R. A Janknegt, C. R.35 Chapple, Eur. Urol. 24: 319-326 (1993)). Longer term studies with terazosin, indoramin, prazosin and doxazosin have similarly demonstrated significant improvements in urinary flow rates and subjective symptom scores (R. A. Janknegt, op. cit., H. Lepor, G. Knapp-Maloney, J. Urol. 40 145: 263A (1991), W. Chow, D. Hahn, D. Sandhu, Br. J. Urol. 65: 36-38 (1990) and C. R. Chapple, T. J. Christmas, E. J. G. Milroy, Urol. Int. 45: 47-55 (1990)). However, these agents possess similar dose-limiting side effects including hypotension, dizziness and muscle fatigue. Pfefferkorn describes an HMC-CoA Reductase compound. The Kleinberg patent describes the inhibition of IGF-1 as a mechanism for the treatment of BPH. The Cox patent describes the formulation of an anti-cancer drug GMC1. The disclosures of the references discussed above are incorporated by reference in their entireties.

In food and nutraceutical capsules containing capsaicin and other capsinoids that produce "heat" in the mouth, the assessment of "heat" since 1912 has been the Scoville scale (Scoville Heat/Thermal Units—SHU/STU). Today the assessment of SHU's is performed with HPLC methodology. McCarty et al in 2015 reported an estimate that 100,000 SHU corresponds to an approximate mixture of capsaicinoids with a combined weight of 6.6 mg. As such, a nutraceutical capsule of powdered Cayenne pepper containing 455 mg of powdered cayenne pepper and assayed to 40,000 SHU would contain 2.64 mg of capsaicinoids. It is worth noting that not all capsinoids produce heat in the mouth due to structural differences in the capsinoid analogues so while the total capsaicinoid weight associated with 40,000 SHUs is about 2.64, the total capsinoid weight could be higher.

As can clearly be appreciated, there is currently a need for a safe method to relieve suffering from urine retention due to bladder outlet obstruction (BOO).

SUMMARY

According to the present invention, and not to be limiting in any way, there is here provided a method for the treatment of bladder outlet obstruction due to benign prostatic hypertrophy comprising administering a therapeutic dose of capsaicin or a capsaicin agonist/analogue.

There is no prior art to suggest that ingestion of large doses of capsaicin or capsaicin agonists/analogues is beneficial to patients suffering from BOO due to BPH.

In preference the cause of the BOO is BPH.

In preference the dose of capsinoids is equivalent to a mg dose of capsaicin or capsaicin agonists or analogues alone or in combination and assayed to 20,000-200,000 Scoville Heat Units (SHU).

This dose is orders of magnitude greater than the dose of powdered capsicum disclosed in US 2010/0204319. In fact, if the capsicum dose in the Archibald publication had been the same as disclosed herein, the synergistic dose would have occurred with the daily ingestion of one (1) capsicum capsule and up to one-hundred (100) broccoli capsules daily. The ingestion of 101 broccoli+capsicum capsules daily is clearly beyond the scope of the Archibald publication as well as being impractical.

In preference the dose of capsinoids is equivalent to a mg dose of capsaicin or capsaicin agonists or analogues alone or in combination and assayed to 40,000 to 80,000 SHUs.

In preference the mg dose of capsaicin is 2-20 mg.

In preference the mg dose of the capsaicin is 5-10 mg.

In preference the mg dose of the capsaicin agonist or analogue is a dose producing an equivalent effect to 2-20 mg of capsaicin on the Scoville Heat Units scale.

A further aspect of the present subject matter is directed to a method for reducing a self-catheterization frequency of a male patient. The method comprises orally administering to a male patient suffering from a bladder outlet obstruction (BOO) due to a benign prostatic hypertropy (BPH) an effective amount, as described above, of an active ingredient selected from a capsinoid mixture that enables the patient suffering from the BOO due to the BPH to reduce the self-catheterization frequency. Another aspect of the present subject matter includes at least one active self-catheterization frequency-reduction ingredient being a synthesized (and not a natural) ingredient.

Still another aspect of the present subject matter involves a case where the capsinoid mixture further includes compounds selected from the group consisting of capsaicin, dihydrocapsaicin, nordihydrocapsaicin, resiniferatoxin (and/or at least one analogous composition thereof), homocapsaicin, homodihydrocapsaicin, and combinations thereof, effective to enable male patients suffering from BOO due to BPH to reduce their self-catheterization frequency.

Still another aspect of the present subject matter involves a case where the capsinoids mixture further includes compounds selected from the group consisting of capsiate, dihydrocapsiate, and nordihydrocapsiate which are all compounds naturally found in chilli peppers and structurally similar to capsaicin.

Yet another aspect of the present subject matter includes capsaicin or compounds of which at least one active self-catheterization frequency-reduction ingredient was synthesized.

DETAILED DESCRIPTION

The following detailed description provides the best currently known modes of carrying out exemplary embodiments of the present subject matter. The following description is therefore not to be taken in a limiting sense, but rather is presented merely to illustrate general principles of the present subject matter since the scope of the present subject matter is best defined by the appended claims found at the end of this detailed description.

In a broad sense, the present subject matter involves providing a method which includes the oral administration of a mixture of capsinoids.

As used herein, the term "effective amount" means an amount of a compound that, when administered to a subject having benign prostatic hypertrophy, is sufficient to effect a reduction in bladder outlet obstruction when present and/or sufficient to effect a reduction in the frequency of self-catheterization necessitated due to a bladder outlet obstruction. The 'effective amount' may vary depending on the compound, the disease and its severity, and the age, co morbidity, weight, social habits such as smoking, alcohol consumption etc., of the subject to be treated.

As used herein, the term "active ingredient" means the ingredient or ingredients that, when administered in an effective amount to a subject having benign prostatic hypertrophy, effects a reduction in bladder outlet obstruction when present and/or effects a reduction in the frequency of self-catheterization necessitated due to a bladder outlet obstruction.

As used herein, the term "capsinoid" refers to both naturally occurring and synthetically produced compounds structurally similar to capsaicin yet are nonpungent in comparison to the perceived heat produced by a like amount of capsaicin.

"Capsinoids" are found naturally present in certain chili peppers. While capsinoids structurally resemble capsaicin, a known substance causing pungency in many hot peppers, capsinoids have an estimated "hot taste threshold" that is about 1/1000th that of capsaicin. Capsinoids weren't reported in the scientific literature, however, until 1989, when biologists first isolated them from a unique variety of chili peppers—CH-19 Sweet—which doesn't contain any capsaicin. Also, the substance "capsinoid" has been found to include capsaicin, dihydrocapsaicin, nordihydrocapsaicin, homocapsaicin, and homodihydrocapsaicin. Capsinoid-like compounds considered analogs of capsaicin include resiniferatoxin and related compounds, which would have similar activity since this is a class effect. Capsinoid compounds are not IGF-1 inhibitors or GMC1 compounds.

Many men currently accept occasional self-catheterization for BOO due to BPH, although current procedures are cumbersome and inconvenient. Indeed, men accept occasional self-catheterization since it delays or avoids the surgical removal of all or part of the prostate gland. The present subject matter advantageously further delays surgical removal of the prostate by reducing bladder outlet obstruction and may be used alone, or in combination with other medications, for this condition. In other words, the method enables a patient suffering from BOO due to BPH to experience a reduced bladder outlet obstruction. The use of this method reduces the frequency of self-catheterization by reducing BOO.

The present subject matter, a method to reduce BOO and frequency of self-catheterization, is a non-hormonal method without adverse side effects of current medications used to reduce BOO in cases of BPH. Current methods often include adrenergic medications and/or male hormone antagonists, with both classes of these drugs known to have adverse side effects. See U.S. Pat. No. 10,010,534 to Cox et al. and U.S. Pat. No. 9,579,364 to Kleinberg et al.

This method, which reduces BOO due to BPH without the degree of side effects associated with current treatments, can be used alone or in combination with the existing medications to result in a decrease in BOO with reduced adverse events. The method enables patients suffering from BOO due to BPH to reduce outlet obstruction and/or self-catheterization frequency.

In greater detail, the present subject matter therefore contemplates the oral administration of a predetermined mix of capsinoids selected to reduce occurrence of bladder outlet obstruction (BOO) in men with benign prostatic hypertrophy (BPH).

Research and Observations Leading to Controlled Experiment

A patient suffering from BOO due to BPH was experiencing increasing symptoms of BOO from 2018 to 2022 in addition to increasing levels of prostate specific antigen (PSA). This patient preferred the occasional self-catheterization to surgical treatment of the BPH. From 2018 to 2021 the self-catheterization frequency associated with 8 mg of silodosin (an alpha-1 antagonist/blocker) orally daily was about once every 6 months. When the dose of silodosin was decreased to 4 mg due to a severe cardiovascular adverse event to the silodosin, the frequency of self-catheterization began to increase. By January 2022, the self-catheterization was weekly. The patient commented that most of the times self-catheterization was necessary, followed a decreased intake of spicy foods, which were an almost daily ingestion for this patient.

EXAMPLE 1

The patient was instructed to ingest 40,000 SHU (Scoville Heat Units) daily in the form of a cayenne nutraceutical capsule obtained over the counter (OTC) at a pharmacy. The cayenne capsule is a powder of ground chili pepper with a claimed total capsinoid activity of 40,000 SHU resulting from the mixture of capsinoid chemicals in the pepper. Not only did the patient report substantial improvement in urine flow but the frequency of self-catheterization was zero over the next 6 months and there was an associated ~15% decrease in the patients PSA suggesting that the prostate size had decreased which was further supported by comparing a previous magnetic resonance image (MRI) to a recent Ultrasound. These clinical findings are consistent with the dramatic improvement in BOO following treatment with oral capsinoids.

EXAMPLE 2

Subsequently, the patient was instructed to double the dose to 40,000 SHU BID which further improved the BOO symptoms.

This is the first time that signs and symptoms of BOO due to BPH have been improved due to oral treatment with high dose capsinoids.

Synthesis of Active Ingredients

The pharmaceutical product (e.g., a cayenne nutraceutical capsule) is from a class of compounds found in nature, which can also be synthesized individually.

The class of chemicals presently described work in a manner that is quite different from adrenergic drugs and their target receptors and indeed quite different from anti-androgen drugs and their target receptors. The present class of chemicals thus targets a class of receptors not currently targeted to treat BOO caused by BPH.

Dosage Levels, Food And Drug Administration (FDA) Considerations for, and Scope of the Present Subject Matter A person of ordinary skill in the art ("POSITA") will appreciate that active ingredients from classes of compounds disclosed can range in potency to reduce BOO and thus can be used individually at varying doses, or as mixtures from nature.

When the method disclosed herein is employed, it is recommended that it is ingested orally once or twice daily. Furthermore, the active ingredients should be manufactured according to FDA standards and regulations. The active ingredients of the disclosed compounds are from a specific class of chemicals that target a specific receptor and are, thus, critical to best medical, safety and health practices.

What has been described in this patent specification is a method of reducing bladder outlet obstruction and the frequency of self-catheterization. While the present subject matter has been described with reference to a single embodiment, the scope of this invention is not limited to this embodiment. On the contrary, many alternatives, changes, and/or modifications will become apparent to a person of ordinary skill in the art ("POSITA") after this patent specification is reviewed. Therefore, all such alternatives, changes, and/or modifications are to be considered as forming a part of the present subject matter insofar as they fall within the spirit and scope of appended claims that follow.

What is claimed is:

1. A method for reducing bladder outlet obstruction of a male patient with BPH, consisting essentially of:
   administering orally to a male patient suffering from a bladder outlet obstruction (BOO) due to a benign prostatic hypertrophy (BPH) a composition consisting of at least one capsaicinoid and/or at least one capsinoid, in an amount equivalent to 20,000-200,000 Scoville Heat Units (SHU), wherein the amount is effective to reduce the bladder outlet obstruction.

2. The method of claim 1, wherein the at least one capsaicinoid and/or the at least one capsinoid is selected from the group consisting of: capsaicin, dihydrocapsaicin, nordihydrocapsaicin, resiniferatoxin homocapsaicin, homodihydrocapsaicin, capsiate, dihydrocapsiate, nordihydrocapsiate, analogous compositions thereto, and any combination thereof.

3. The method of claim 1, wherein the at least one capsaicinoid and/or at least one capsinoid is selected from the group consisting of capsaicin, a capsaicin agonist, a capsaicin analogue, and any combination thereof.

4. The method of claim 1, wherein the at least one capsaicinoid and/or capsinoid includes a synthesized capsaicinoid and/or a synthesized capsinoid.

5. The method of claim 4, wherein the composition excludes naturally occurring capsaicinoid and/or capsinoid compounds.

6. The method of claim 1, wherein the amount is equivalent to 40,000 to 80,000 SHU.

7. The method of claim 1, wherein the amount is equivalent to 2-20 mg of capsaicin.

8. The method of claim 1, wherein the amount is equivalent to 5-10 mg capsaicin.

9. A method for reducing bladder outlet obstruction of a male patient with BPH, consisting essentially of:
   administering orally to a male patient suffering from a bladder outlet obstruction (BOO) due to a benign prostatic hypertrophy (BPH) a composition consisting of at least one capsaicinoid and/or at least one capsinoid, in an amount equivalent to 2-20 mg of capsaicin, wherein the amount is effective to reduce the bladder outlet obstruction.

10. The method of claim 9, wherein the at least one capsaicinoid and/or the at least one capsinoid is selected from the group consisting of: capsaicin, dihydrocapsaicin, nordihydrocapsaicin, resiniferatoxin homocapsaicin, homodihydrocapsaicin, capsiate, dihydrocapsiate, nordihydrocapsiate, analogous compositions thereto, and any combination thereof.

* * * * *